US006168794B1

(12) United States Patent
Reusser et al.

(10) Patent No.: US 6,168,794 B1
(45) Date of Patent: Jan. 2, 2001

(54) COMPOSITIONS COMPRISING OLEUM MELALEUCA

(75) Inventors: Kenneth L. Reusser; Gertrude G. Reusser, both of Beaverton; Michael J. Schmidt, Portland, all of OR (US)

(73) Assignee: Safe 'N Sound Solutions, Inc., Beaverton, OR (US)

( * ) Notice: Under 35 U.S.C. 154(b), the term of this patent shall be extended for 0 days.

(21) Appl. No.: 09/185,378

(22) Filed: Nov. 3, 1998

(51) Int. Cl.$^7$ ................................................ A61K 35/78
(52) U.S. Cl. ............................................................ 424/195.1
(58) Field of Search ........................................... 424/195.1

(56) References Cited

U.S. PATENT DOCUMENTS

| | | | |
|---|---|---|---|
| 5,009,890 | 4/1991 | DiPippo | 424/195.1 |
| 5,096,709 | 3/1992 | Vandersloot | 424/195.1 |
| 5,385,733 | 1/1995 | Mankovitz | 424/195.1 |
| 5,449,517 | 9/1995 | Fitzjarrell | 424/195.1 |
| 5,738,863 | 4/1998 | Sackin et al. | 424/405 |
| 5,774,909 | * 7/1998 | Stable | 4/622 |

FOREIGN PATENT DOCUMENTS

| | | |
|---|---|---|
| 559001 | * 2/1987 | (AU) . |
| 19631037 | * 2/1998 | (DE) . |
| 9110364 | * 7/1991 | (WO) . |
| 9735558 | * 10 1997 | (WO) . |

OTHER PUBLICATIONS

Bakker et al., International Journal of Dermatology 31(3): 210–213 (Mar. 1992). Abstract.*

Pildes et al., J Pediat. 82(6): 987–990 (1973). Abstract.*

Hammer et al., American Journal of Infection Control 24(3): 186–189 (Jun. 1996).*

CA Registry 39389–84–9 "Brilliant Green–proflavine hemisulfate–crystal violet mixture".*

Humphery, "A New Australian Germicide," *The Medical J. of Australia*, 1:417–418 (1930).

Swords and Hunter, "Composition of Australian Tea Tree Oil (*Melaleuca alternifolia*)," *J. of Agric.I Food Chem.*, 26:734–737 (1978).

Carson et al., "Susceptibility of Methicillin–resistant *Staphylococcus aureus* to the Essential Oil of *Melaleuca alternifolia*," *Journal of Antimicrobial Chemotherapy*, 35:421–424 (1995).

Nenoff et al., "Antifungal Activity of the Essential Oil of *Melaleuca alternifolia* (Tea Tree Oil) Against Pathogenic Fungi in vitro," *Skin Pharmacol*, 9:388–394 (1996).

Hammer et al., "Susceptibility of Transient and Commensal Skin Flora to the Essential Oil of *Melaleuca alternifolia* (Tea Tree Oil)," *Association of Professionals in Infection Control and Epidemiology, Inc.*, 24:186–189 (1996).

* cited by examiner

*Primary Examiner*—Jean C. Witz
(74) *Attorney, Agent, or Firm*—Klarquist Sparkman Campbell Leigh & Whinston, LLP

(57) ABSTRACT

Compositions comprising oleum *Melaleuca alternifolia*, water-soluble oleum *Melaleuca alternifolia*, antimicrobial agents, carriers and mixtures thereof are described. The invention also comprises methods for using the compositions to treat animals, particularly for treating lesions.

13 Claims, 3 Drawing Sheets

COMPOSITIONS COMPRISING OLEUM MELALEUCA

FIELD OF THE INVENTION

This invention concerns compositions comprising oleum Melaleuca and methods for using the compositions to treat lesions.

BACKGROUND OF THE INVENTION

A. Disease in Animals

Lameness in animals can lead to death or a decrease in the commercial value of the animal. There are multiple causes for the condition ranging from genetic defects to bacterial and viral infections. For example, *fibroma* (corns) is a genetic condition found in cattle which causes a hard, fibrous lump to form between the claws of the foot. The corn makes the hoof more susceptible to subsequent bacterial and viral infections. These infections occur at various locations in and around the hooves of the cattle. Greenough et al., *Lameness in Cattle* 3$^{rd}$, (1996).

In addition to the general lesions caused by infection, a disease of unknown etiology has been spreading throughout the western United States. This disease is digital dermatitis (DD). DD is characterized by painful lesions, which often are surrounded by a ridge of hyperkeratotic (thickened) skin with finger like projections. For this reason, the disease is commonly referred to as hairy wart.

DD is contagious and has spread rapidly throughout cattle herds in the United States. A survey of cattle owners showed that 17.2% of cows and 6–8% of bred heifers in the 12 months before Feb. 20, 1996, showed signs of the disease. USDA Papillomatous Digital Dermatitis on U.S. Dairy Operations (1997). In addition to causing lameness in cattle, DD also causes decreased milk production and sometimes death. Dairy farmers report as much as 50% less milk being produced per cow. Linda Leake, Farm Journal, Inc., (1998).

Currently, cattle are being treated for lameness using antibiotics, topically applied caustic compounds and/or foot baths containing formaldehyde or tetracycline. While these treatments are useful, they also introduce unwanted contaminants into the food chain. The use of tetracycline on dairy cattle, for example, can lead to the production of contaminated milk having little-to-no commercial value. The FDA has restricted the use of several antibiotics, including streptomycin, chloramphenicol, tetracycline and penicillin. Nevertheless, in order to achieve rapid healing and to avoid loss of income, prohibited antibiotics may be misused.

B. Oleum *Melaleuca alternifolia*

Oil extracted from the Australian tea tree (oleum *Melaleuca alternifolia*) has been used by the aboriginal people since before the first european settlers arrived. One of the first published reports concerning the oil identified its germicidal qualities as being 11–13 times more effective than phenol. Dr. E. M. Humphrey, *MJA;* 1:417–418 (1930).

In 1978 a list was compiled of 48 different compounds found in oleum *Melaleuca alternifolia*. Greg Swords & G. L. K. Hunter, *J. of Agricultural Food Chemistry,* 26:3, pp. 734–737 (1978). See, Table 1 below. Of these compounds, terpinen-4-ol is considered to be the most active ingredient, but experiments using terpinen-4-ol alone have shown that it is not nearly as effective as the complete oil. Purity and effectiveness of the extracted oil is determined by the terpinen-4-ol content and cineole content. Typically, high quality oil includes up to 60% terpinen-4-ol and less than 10% cineole.

TABLE 1

| Compound | Fraction | Evidence for | Percent of |
|---|---|---|---|
| 1. $_{OL}$-Pinene | 0,$^a$ 2–5 | GC MS | 2.8 |
| 2. Camphene | 2 | GC MS | Tr |
| 3. $_a$-Pinene | 0, 2–4 | GC MS | 0.59 |
| 4. Sabinene | 0 | GC MS | 0.12 |
| 5. Myrcene | 0, 2–5 | GC MS | 0.52 |
| 6. $_{OL}$-Phellandrene | 0, 2–5 | GC MS | 0.11 |
| 7. 1,4-Cineole | 5, 6 | GC MS | Tr |
| 8. $_{OL}$-Terpinene | 0, 2–5 | GC MS | 2.74 |
| 9. Limonene | 0, 2–5 | GC MS | 3.09 |
| 10. 1,8-Cineole | 0, 5–7 | GC MS | 16.50 |
| 11. y-Terpinene | 0, 2–5 | GC MS | 11.54 |
| 12. p-Cymene | 0, 2–7 | GC MS | 11.42 |
| 13. Terpinolene | 0, 2–6 | GC MS | 2.36 |
| 14. Hexanol | 7 | GC MS | Tr |
| 15. Allyl hexanoate | 6, 7 | GC MS | Tr |
| 16. p, $_{OL}$ | 0, 5–7 | GC MS | 0.07 |
| 17. a Sesquiterpene | 0, 2, 3 | GC MS | Tr |
| 18. $_{OL}$-Cubebene | 2, 3 | GC MS$_{1,2}$ | 0.04 |
| 19. a Sesquiterpene | 2–4 | GC MS | Tr |
| 20. $_{OL}$-Copaene | 0, 2–4 | GC MS | 0.10 |
| 21. Camphor | 6, 7 | GC MS | Tr |
| 22. $_{OL}$-Gurjunene | 0, 2–4 | GC$_3$ MS$_2$ IR$_4$ | 0.23 |
| 23. Linalool | 6, 7 | GC MS | 0.10 |
| 24. a Sesquiterpene | 2, 3 | GC MS | Tr |
| 25. Unidentified | 6, 7 | | 0.05 |
| 26. 1-Terpineol | 6 | GC MS | Tr |
| 27. 1-Terpinen-4-ol | 0, 6, 7 | GC MS | 29.41 |
| 28. $_a$-Eiemene | 3–5 | GC MS$_{1-5}$ | Tr |
| 29. Caryophyllene | 3–5 | GC MS$_1$ | Tr |
| 30. a Sesquiterpene | 3–5 | GC MS | 0.06 |
| 31. Aromadendrene | 2–5 | GC MS$_2$ IR$_6$ | 2.35 |
| 32. $_a$-Terpineol | 6, 7 | GC MS | 0.24 |
| 33. Alloaromadendrene | 2–5 | GC MS$_2$ IR$_6$ | 0.45 |
| 34. Unidentified | 6, 7 | | 0.27 |
| 35. Humulene | 4–6 | GC MS | Tr |
| 36. Unidentified | 6, 7 | | Tr |
| 37. y-Muurolene | 2–4 | GC$_3$, MS$_2$ | Tr |
| 38. $_{OL}$-Terpineol | 0, 5–7 | GC MS | 3.61 |
| 39. Viridiflorene | 0, 2–4 | GC MS IR$^7$ NMR | 1.03 |
| 40. Piperitone | 7 | GC MS | 0.08 |
| 41. $_{OL}$-Muurolene | 2–4 | GC$^3$ MS$^2$ IR$^6$ | 0.12 |
| 42. Piperitol | 7 | GC MS | 0.07 |
| 43. Unidentified | 7, 8 | | 0.07 |
| 44. $_o$-Cadinene | 0, 2–4 | GC$^3$ MS$^2$ IR$^4$ | 1.43 |
| 45. 4,10-Dimethyl-7-isopropyl bicyclo [4.4.0]- | 4 | MS$_2$ | 0.10 |
| 46. Nerol | 7 | GC MS | Tr |
| 47. 8-p-Cymenol | 6, 7 | GC MS | 0.13 |
| 48. Calamenene | 0, 2–5 | GC$_{8,9}$ MS$_5$ IR$_{4,5}$ | 0.10 |

$^a$0 refers to the whole oil.
$^b$1, Moshanas and Lund (1970); 2, Stenhagen et al. (1970); 3, Andersen and Falcone (1969); 4, Wenninger et al. (1967); 5, Yukawa and Ito (1973); 6, Wenninger et al. (1970); 7, Serkebaeva et al. (1968); 8, Lawrence et al. (1960); 9, Yates and Wenninger (1970).
MS refers to mass spectrometry.
IR refers to infrared spectroscopy,
NMR refers to nuclear magnetic resonance spectroscopy, and
GS refers to gas spectrometry.

Oleum *Melaleuca alternifolia* has been combined with aloe and used to suppress flea infestation in domestic animals. See, Fitzjarrall's U.S. Pat. No. 5,449,517. Oleum *Melaleuca alternifolia* also has been combined with butylated hydroxy toluene to suppress herpes lesions, menthol to relax muscles, gum to treat burns, and benzaldehyde to repel stinging insects. See, Mankovitz's U.S. Pat. No. 5,385,733, VanderSloot's U.S. Pat. No. 5,096,709, DiPippo's U.S. Pat. No. 5,009,890, and Sackin's U.S. Pat. No. 5,738,863, respectively.

Additional research has shown that oleum *Melaleuca alternifolia* inhibits fungal and bacterial growth. A minimum inhibitory concentration (MIC) for fungal growth was determined using agar dilution techniques, and a MIC for bacteria determined using disc diffusion. These MICs were from about 0.4% to about 0.5% for fungi and from about 0.2% to about 0.5% for Staphylococcus aureus. Nenoff et al., *Skin Pharmacol.*, 9:6, pp. 388–944 (1996), and Carson et al., *J. Antimicrob. Chemother.*, 35:3, pp. 421–424 (1995), respectively.

SUMMARY OF THE INVENTION

The present invention provides compositions containing oleum Melaleuca, and methods for using such compositions. Particular compositions, referred to herein as MSC compositions, comprise oleum *Melaleuca alternifolia*, a water-soluble form of oleum *Melaleuca alternifolia* and a carrier. In a working embodiment, the carrier was glycerin and the water-soluble form of oleum *Melaleuca alternifolia* was Sol-U-Mel®.

The concentrations of each of the individual components can vary. Using 100% oleum *Melaleuca alternifolia* to treat livestock lesions is not preferred because it requires multiple applications per day to effectively treat the lesions. The concentration of the oleum *Melaleuca alternifolia* and the water-soluble form of oleum *Melaleuca alternifolia* in the MSC composition generally range from about 2% by weight to about 50% by weight relative to the total weight of the MSC composition (unless stated otherwise, all percent values stated herein are relative to the total weight of the particular composition being discussed). The remainder of the MSC composition typically is glycerin, but such compositions also can include additional materials useful for providing therapeutic compositions. In one working embodiment, the composition comprised about 13.8% by weight oleum *Melaleuca alternifolia*, about 12.7% by weight Sol-U-Mel® and about 73.5% by weight glycerin.

The invention also provides a method for treating animals, particularly for treating lesions, using embodiments of the MSC composition. "Animal" as used herein shall mean all mammals, but generally not humans, and typically refers to livestock such as cattle. The method comprises providing an MSC composition, and contacting the lesion with a therapeutically effective amount of the composition for a therapeutically effective period of time.

The MSC composition also can be used in combination with a bandage, such as the working embodiment illustrated in FIG. 1. This bandage comprised an absorptive material having a resilient backing. The absorptive material maintains the composition in contact with the animal, such as over and about lesions, for a therapeutically effective period of time. The resilient material helps flow the MSC composition on, into and about lesions.

The present invention also provides compositions that are particularly useful for treating DD. These compositions comprise oleum *Melaleuca alternifolia*, a water-soluble form of oleum *Melaleuca alternifolia*, at least one additional antimicrobial agent, typically a carrier, and perhaps other materials that are useful for forming compositions for treating DD. In one working embodiment, the carrier was glycerin, the water-soluble form of oleum *Melaleuca alternifolia* was Sol-U-Mel®, and the antimicrobial agent was selected from the group consisting of Brilliant Green, Gentian Violet, Proflavine hemisulfate, and mixtures thereof.

The concentrations of each of the individual components in the DD composition can vary. DD compositions typically comprise at least about 0.2% to about 50% by weight oleum *Melaleuca alternifolia*, and from about 0.2% to about 50% by weight water-soluble form of oleum *Melaleuca alternifolia*. The concentrations of Brilliant Green and Gentian Violet generally vary from about 0.05% to about 5% by weight, and preferably from about 0.2% to about 0.5% by weight. The concentration of Proflavine hemisulfate typically ranges from about 0.01% by weight to about 5% by weight, and preferably from about 0.1% to about 0.5% by weight. The total amount of Brilliant Green, Gentian Violet and Proflavine hemisulfate typically is less than about 1% by weight. The remainder of the composition comprises a carrier, particularly glycerin, and perhaps other materials useful for forming compositions for treating DD. In one working embodiment, the DD composition comprised about: 73% by weight glycerin; 13.8% by weight oleum *Melaleuca alternifolia*; 12.7% by weight Sol-U-Mel®; 0.2% by weight Gentian Violet; 0.2% by weight Brilliant Green; and 0.1% by weight Proflavine hemisulfate.

The invention also provides a method for treating DD. This method comprises contacting lesions with therapeutically effective amounts of embodiments of the DD composition for a therapeutically effective period of time. The composition can be used in combination with a bandage as described above for use in combination with the MSC composition.

DETAILED DESCRIPTION OF THE PREFERRED EMBODIMENTS

I. Definitions

Figure 1:
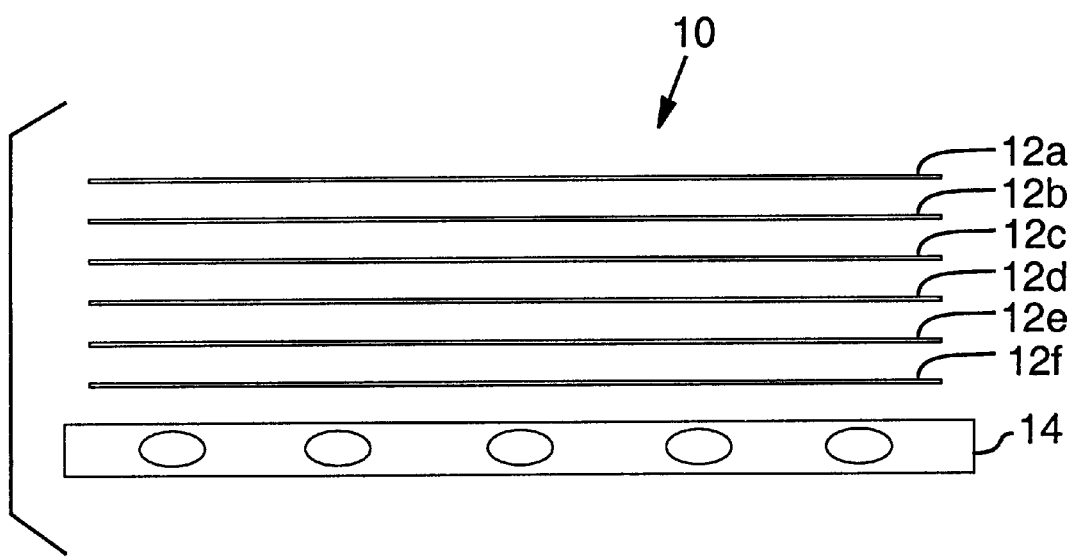
FIG. 1 is a diagram illustrating one embodiment of a bandage for use with compositions of the present invention.
Figure 2:
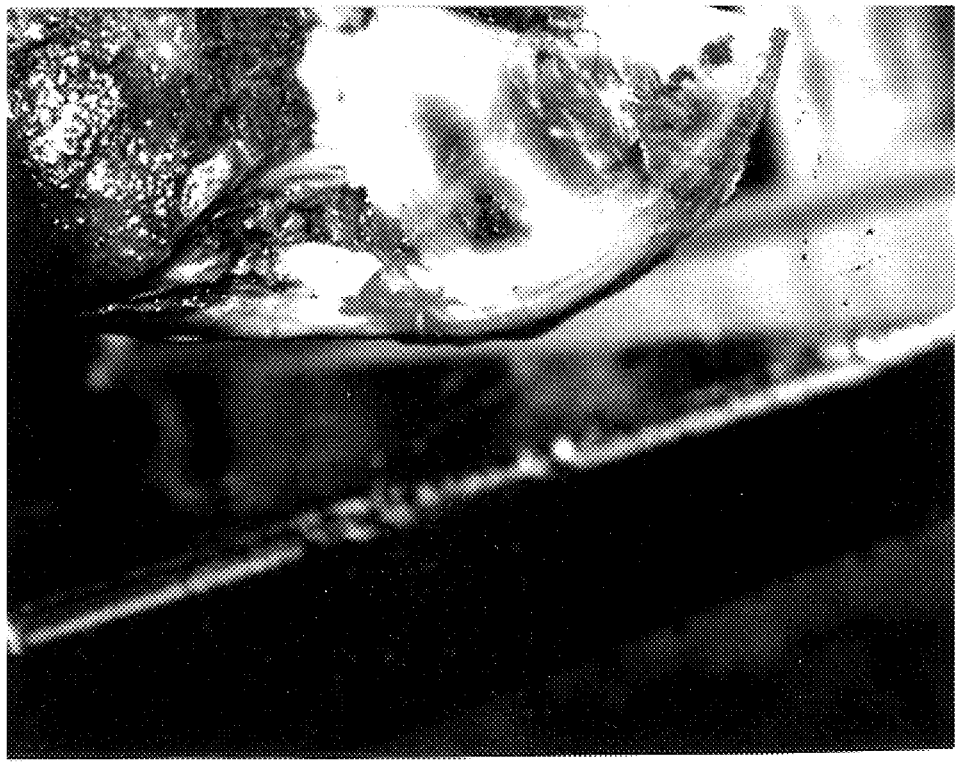
FIG. 2 is a photograph of a cow's foot having an abscess.
Figure 3:
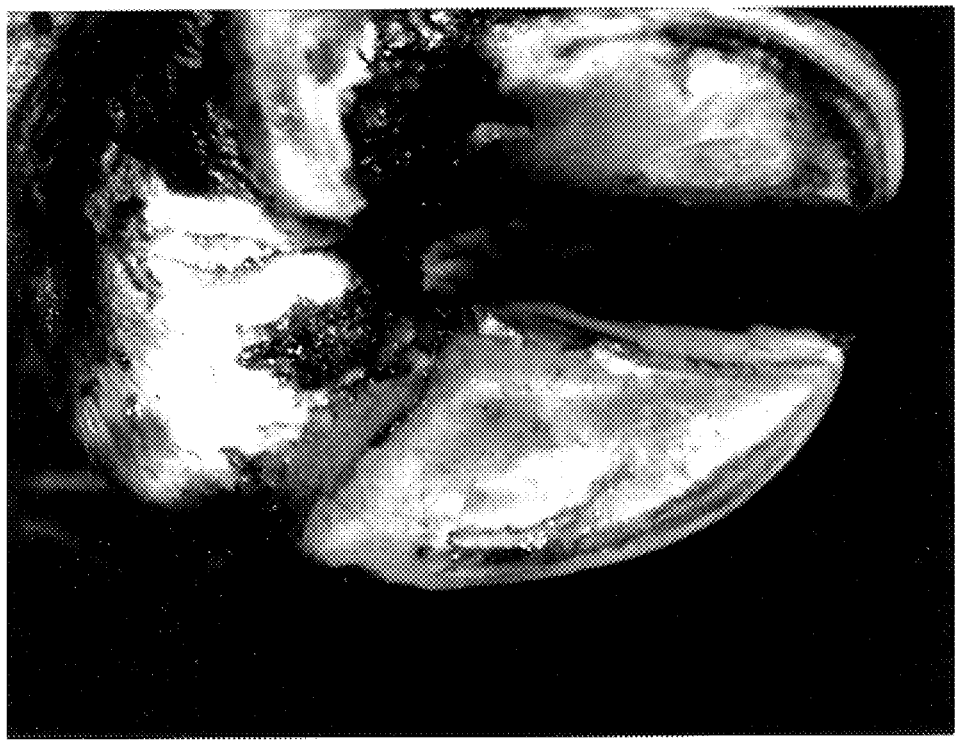
FIG. 3 is a photograph of the same cow's foot of FIG. 2 following treatment with a therapeutic composition of the present invention.
Figure 4:
FIG. 4 is a photograph of a cow's foot having digital dermatitis.
Figure 5:
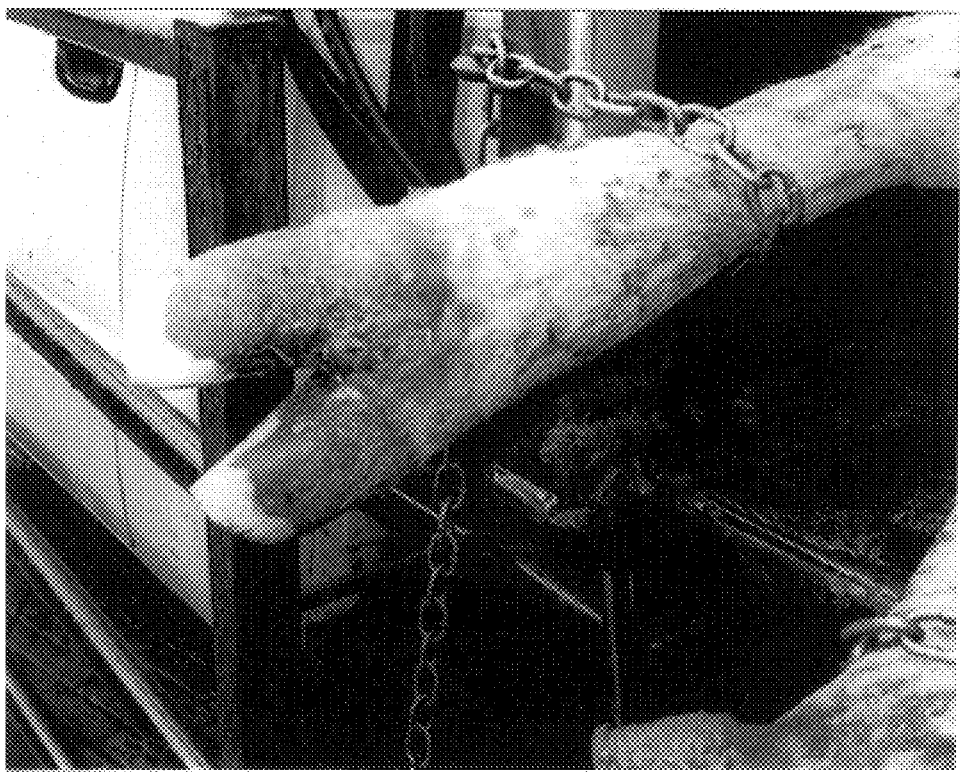
FIG. 5 is a photograph of the foot of FIG. 4 following treatment with a therapeutic composition of the present invention.

Therapeutically effective period of time: The amount of time necessary for a lesion to substantially cease excreting fluids, become less inflamed and initialize repair of the epithelium. This time period typically is from about 24 hours to about 6 days. Longer time periods, however, might be necessary if the lesion is severe and shorter time periods might be applicable for minor lesions.

Therapeutic composition: A composition comprising oleum Melaleuca according to the present invention capable of causing substantial cessation of fluid excretion, reduction of inflammation and initialization of epithelium repair.

Therapeutically effective amount: An amount of a composition sufficient for causing substantial cessation of fluid excretion, reduction of inflammation and initialization of endothelium repair. The amount depends on the subject being treated, the severity of the affliction, and the manner of administering the composition. The therapeutic can be administered in a range of from about 5 ml to about 100 ml, and more typically in a range of from about 20 ml to about 50 ml.

Carrier: A compound which facilitates the delivery of oleum Melaleuca to the affected area.

Abscess: Acute product of bacterial infection. Lesions present in abscesses are characterized by the excretion of fluids that are transudates or exudates (clear or pus) and active inflammation.

Ulcer: Chronic lesion from injury, such as an abrasion caused by rubbing against objects in the animal's environment. Lesions present in ulcers are characterized by a lack of acute inflammation and excreted matter.

Laminitis: Damage to the blood vessels that are responsible for the production of the claw horn. Therefore, the claw horn is deteriorated and becomes damaged.

Foot Rot: Highly infectious bacterial disease that is characterized by an infection of the skin between the claws.

II. Composition

A. Oleum *Melaleuca alternifolia*

There are several obstacles that must be overcome to effectively treat lesions in animals. Often the animals are kept in conditions which cause them to be in contact with urine and fecal matter. These conditions therefore lead to an increased exposure and susceptibility to microorganisms, such as bacteria, fungi and viruses. In addition to these problems, ranchers and dairy farmers must be able to isolate and treat animals from large herds. Therefore, it is desirable to have a therapeutic agent which can successfully treat disease without the need for multiple applications.

Compositions comprising oleum *Melaleuca alternifolia* are effective therapeutics which can work under the conditions described above. The oil has very low toxicity, and is generally non-irritating even to sensitive tissues.

The tree known as *Melaleuca alternifolia* is one of over 100 species found in the genus Melaleuca. These species were originally found in Australia and have since been successfully grown in various places around the world. One of ordinary skill in the art will appreciate that other members of the genus Melaleuca may produce an oil having a composition that is substantially similar to oleum *Melaleuca alternifolia* or having therapeutic effects substantially similar to those of oleum *Melaleuca alternifolia*. Therefore, compositions that include oleum *Melaleuca alternifolia* are just one representative type of therapeutic composition, and other embodiments can include oil derived from plants within the genus Melaleuca.

As mentioned above, oleum *Melaleuca alternifolia* has been found to contain at least those 48 different components listed in Table 1. Of those components, 2 typically have been used to characterize the quality of the oil, 1,8-cineole and terpine-4-ol. The 1,8-cineole content can effect the oils ability to penetrate tissue, but also produces tissue irritation in concentrations above 10%. Accordingly, it is preferable to maintain the 1,8-cineole concentration below about 10%, preferably below about 7%. It also is generally believed that the terpinen-4-ol content assists in the healing of damaged tissue, and concentrations of 35% or more of this compound are desirable.

One or more of the individual components of the oleum Melaleuca oil may be deleted and/or substituted. The deletion of one or more of the components could be done such that the therapeutic functionality of the oil is maintained. It also is likely that one or more of the components could be substituted with a functionally similar component. Therefore, the scope of the present invention encompasses deletion and/or substitution variants of oleum *Melaleuca alternifolia*.

It has been found that 100% oleum *Melaleuca alternifolia* promotes healing after one application. However, multiple applications per day would be required to fully heal a lesion. Therefore, 100% oleum *Malaleuca alternifolia* was determined to be not ideal for treating lesions because it required repeated isolation of the diseased animal from the herd and multiple applications of the therapeutic.

Oleum *Melaleuca alternifolia* previously has been found to be effective for inhibiting bacterial growth at a concentration of about 0.2%. Nenoff et al., supra, (1996).

Additionally, experiments have shown that 100% oleum *Melaleuca alternifolia* is capable of promoting healing (data not shown). Therefore, compositions useful for promoting healing and curtailing infection can comprise from about 0.2% to about 100% by weight oleum *Melaleuca alternifolia*. But, such compositions typically include oleum *Melaleuca alternifolia* in amounts of from about 0.2% to about 50% by weight, preferably from about 5% by weight to about 25% by weight, and more preferably from about 10% to about 20% by weight.

B. Water-soluble Form of oleum *Melaleuca alternifolia*

Substantially pure oleum *Melaleuca alternifolia* compositions are partially insoluble in water. Compositions of the present invention preferably also include a more water-soluble form of oleum *Melaleuca alternifolia*. The aqueous solubility of the oil can be enhanced by forming mixtures comprising additional components, such as surfactants. One example, without limitation, of a suitable surfactant is polyoxylethylene sorbitan mono-oleate.

In a working embodiment, the commercially available water-soluble form of oleum *Melaleuca alternifolia* was Sol-U-Mel®. Sol-U-Mel® can be 10 purchased from Melaleuca, Inc., 3910 South Yellowstone Hwy., Idaho Falls, Id. USA 83402.

In another working embodiment, the water-soluble form of oleum *Melaleuca alternifolia* was solubilized using green soap and alcohol. Typically, from about 10% by weight to about 50% by weight green soap, and from about 50% by weight to about 90% by weight ethyl alcohol was added to the oleum *Melaleuca alternifolia*. This provides a stock solution that can be mixed with other components to form the therapeutic composition.

There are several benefits associated with increasing the aqueous solubility of oleum *Melaleuca alternifolia*. For example, solubilizing the oil allows the formation of aqueous mixtures comprising additional aqueous soluble, miscible or suspendable compounds. These compounds can be chosen such that they enhance therapeutic activity. Therefore, the amount of aqueous solublized oleum *Melaleuca alternifolia* used will depend on the component or components it is mixed with, and the proposed use of the composition. Compositions currently considered useful for treating topical lesions typically comprise from about 0.2% to about 50% by weight, preferably from about 5% to about 25% by weight, and more preferably from about 10% to about 20% by weight aqueous soluble oleum *Melaleuca alternifolia*.

C. Carrier

The compositions of the present invention generally include a carrier, which facilitates delivering the oil to the lesion. The particular carrier used will depend on the specific type of application. For example, a preferred carrier for topical applications is one that does not cause excessive softening of the tissue around the lesion.

Preferred carriers for topical applications are both humectants and hygroscopics. Hygroscopic substances absorb moisture. The absorption of moisture allows these substances to form gels that facilitate delivery of the therapeutic to the desired location. Examples of hygroscopic compounds include glycerin, cellulose, silica gel, calcium chloride and zinc chloride. In addition to absorbing water, many hygroscopic compounds also are humectants. A humectant absorbs water, but also has the ability to keep the moisture content of a material within a particular range. This is desirable for topical applications in which complete drying of the tissue is not desired.

In a working embodiment the carrier was glycerin (also referred to as glycerol). Glycerin is both a humectant and hygroscopic, and furthermore is a relatively viscous liquid that is soluble in water and alcohol. The viscosity of glycerin apparently enhances the penetration of the therapeutic compositions of the present invention into tissue while not causing excessive softening of the tissue to which it is applied.

Selecting carriers for use with other delivery methods depends on the particular mode of administration used. For instance, formulations used for the purpose of irrigating lesions usually comprise fluids that include pharmaceutically and physiologically acceptable fluids such as water, physiological saline, balanced salt solutions, aqueous dextrose, glycerol, and mixtures thereof. For solid compositions (e.g., powder, pill, tablet, or capsule forms), conventional non-toxic solid carriers can include, for example, pharmaceutical grades of mannitol, lactose, starch, magnesium stearate and mixtures thereof.

D. Additional Antimicrobial Agents

Mixtures comprising oleum *Melaleuca alternifolia*, water-soluble oleum *Melaleuca alternifolia*, and a carrier have proved to be effective for treating abscesses, ulcers, laminitis, foot rot, and bruises. They have not, however, proved to be completely effective for treating DD.

The addition of an antiseptic agent or agents to compositions comprising oleum *Melaleuca alternifolia*, particularly compositions comprising oleum *Melaleuca alternifolia*, a water-soluble oleum *Melaleuca alternifolia*, and generally a carrier, forms a mixture substantially more effective for treating DD. In a working embodiment, the antiseptic agent was a combination of three dyes. These dyes were N-[4-[[4-(Diethylamino)phenyl]-phenylmethylene]-2,5-cyclohexadien-1-ylidene]-N-ethylethanaminium sulfate (1:1) (Brilliant Green), N-[4[Bis[4-(dimethylamino)-phenyl]methylene]-2,5-cyclohexadien-1-ylidene]-N-methyl-methanaminium chloride (Gentian Violet), 3,6-Acridinediamine hemisulfate (Proflavine hemisulfate), and various mixtures thereof. The concentration of Brilliant Green typically ranges from about 0.05% to about 5% by weight, more typically from about 0.1% to about 1% by weight, and preferably from about 0.1% to about 0.5% by weight. The concentration of Gentian Violet typically varies from about 0.05% to about 5% by weight, typically from about 0.1% to about 1% by weight, and preferably from about 0.1% to about 0.5% by weight. The concentration of Proflavine hemisulfate typically ranges from about 0.01% by weight to about 5% by weight, and preferably from about 0.05% to about 0.5% by weight. The amounts of Brilliant Green, Gentian Violet and Proflavine hemisulfate in working embodiments of DD compositions typically totaled less than about 5%, more typically less than about 1% and preferably about 0.5% by weight.

E. Other Materials that are Useful for Forming Therapeutic Compositions

In addition to biologically-inactive carriers, the above mentioned compositions can include other, generally non-toxic auxiliary substances, as long as such substances do not detract from the benefits provided by the present therapeutic compositions. These materials include wetting or emulsifying agents, preservatives, excipients, pH buffering agents, other therapeutics that do not contaminate meat or dairy products produced by the animal, and mixtures thereof. These agents, may for example, facilitate the delivery and efficiency of the therapeutic agent.

III. Using the Composition

The compositions of this invention may be used to irrigate a lesion or as a topically applied therapeutic. Administration of the composition is indicated for animals which have been injured or infected. The particular mode of administration and the dosage regimen will be selected by the care giver, taking into account the particulars of the case (e.g., the disease, and the disease state involved). For instance, if the lesion is a subdermal abscess the desired mode of administration might be through irrigation of the affected area. In contrast, minor abrasions of the epidermal layer might be treated with a single topical application of the composition.

Compositions comprising oleum *Melaleuca alternifolia* can be applied topically with or without a bandage. The use of a bandage provides multiple benefits. A bandage serves to keep the fecal matter and urine of the environment away from the affected tissue and also maintains the composition in contact with the affected site for a therapeutically effective period of time.

Working bandages have the capability of absorbing the composition and delivering it to the affected site. This can be accomplished by using a bandage which has an absorptive layer. After the lesion is cleansed the composition can then be applied directly to the lesion and/or the absorptive layer of the bandage. Once in place the bandage then serves to provide continued delivery of the composition. The bandage can be further improved by including a resilient backing layer.

FIG. 1 illustrates one embodiment of such a bandage 10. Bandage 10 includes at least one absorptive layer 12, and perhaps plural such layers 12a–f, and a resilient layer 14. In a working embodiment, the resilient layer 14 was made of bubble wrap and the absorptive layer 12a–f was rolled cotton. The resilient layer 14 contacts absorptive layer 12a. Absorptive layer 12f contacts the animal when bandage 10 is used and the resilient layer 14 covers the absorptive layers 12a–f. Resilient layer 14 serves several purposes. For example, it decreases evaporation of the composition. Second, it causes the composition to be pumped into the lesion when the animal moves by repeated compression and expansion of the resilient material. This pumping action results from pressure between the flexing muscles of the animal and the resilient material and it allows the composition to penetrate farther on, into and about the lesion.

IV. Summary of Results

A. Composition Containing Oleum *Melaleuca alternifolia*, Water-Soluble *Melaleuca alternifolia* and a Carrier The composition containing oleum *Melaleuca alternifolia*, water-soluble oleum *Melaleuca alternifolia*, and a carrier was applied to 514 cattle (Table 2). The lesions treated were characterized as abscesses, ulcers or DD. The results were recorded as: excellent response, good response or poor response. Lesions classified in the excellent category did not require further application of the composition. Lesions classified in the good category required further applications in order to have complete recovery. Finally, lesions which responded poorly were not given further treatments.

Of the 340 cattle treated for abscess, 315 showed an excellent response to the treatment. The 25 remaining cattle showed a good response to the treatment. Most important, 100% of the cattle treated with this composition recovered.

Of the 112 cattle treated for ulcers, 95 showed an excellent response to the treatment. The 17 remaining cattle showed a good response to the treatment. Thus, the results were similar to those seen in the treatment of abscess in that 100% of the cattle treated recovered.

Of the 5 cattle treated for foot rot, 5 showed an excellent response to the treatment. Therefore, 100% of the cattle recovered.

Laminitis was also successfully treated with the MSC composition. There were 57 cattle treated and all 57 showed an excellent response.

The treatment group containing cattle displaying signs of DD did not respond well to the MSC composition. There were 77 cattle treated and 9 of those showed an excellent response, and 1 showed a good response. The remaining 72 fell into the poor response category and treatment was not continued.

TABLE 2

Response to Composition Comprising Oleum *Melaleuca alternifolia*, Water-soluble Oleum *Melaleuca alternifolia*, and Glycerin.

| Problem | Total Number | Response | Excellent (%) | Good (%) | Poor (%) |
| --- | --- | --- | --- | --- | --- |
| Abscess | 340 | | 315 (93) | 25 (7) | 0 (0) |
| Ulcer | 112 | | 95 (85) | 17 (15) | 0 (0) |
| Foot Rot | 5 | | 5 (100) | 0 | 0 |
| Laminitis | 57 | | 57 (100) | 0 | 0 |
| Hairy Wart* | 77 | | 9 (10) | 1 (2) | 72 (88) |
| TOTAL: | 514 | | | | |

*discontinued treatments due to poor results

B. Composition Containing Oleum *Melaleuca alternifolia*, water-soluble *Melaleuca alternifolia*, an Antimicrobial agent and a Carrier The composition was applied to 310 cattle (Table 3). Of these cattle, 294 showed an excellent response and did not need to have a second treatment. The remaining 16 cattle showed a good response after the initial treatment and where subsequently cured with an additional treatment.

TABLE 3

Response to Composition Comprising, Oleum *Melaleuca alternifolia*, Water-soluble Oleum *Melaleuca alternifolia*, Gentian Violet, Brillant Green, Proflavine Hemisulfate, and Glycerin.

| Problem | Total Number | Response | Excellent (%) | Good (%) | Poor (%) |
| --- | --- | --- | --- | --- | --- |
| DD | 310 | | 294 (95) | 16 (5) | 0 (0) |

EXAMPLE 1

This example describes a method for making compositions comprising oleum *Melaleuca alternifolia*, water-soluble *Melaleuca alternifolia* and a carrier. Substantially pure glycerin was obtained. Sol-U-Mel® and oleum *Melaleuca alternifolia* were both obtained from Melaleuca, Inc., 3910 South Yellowstone Hwy., Idaho Falls, Id. USA 83402. 19 ml glycerin, 6 ml oleum *Melaleuca alternifolia* and 5 ml Sol-U-Mel® were added to a high shear mixer and then mixed to provide a substantially homogenous composition.

EXAMPLE 2

This example describes a method for treating lesions using compositions comprising oleum *Melaleuca alternifolia*, water-soluble *Melaleuca alternifolia* and a carrier. The animal to be treated was identified by the name of the farm and the identification tag on the animal. Lesions were then identified as either an abscess or an ulcer. This information was recorded along with the date of treatment.

The lesion was cleansed with Tough 'n Tender, an antibacterial all purpose cleanser, available from Melaleuca, Inc and an additional antibiotic liquid soap. The composition described in Example 1 was then topically applied to the lesion. Amounts of the composition applied to the wound varied depending upon the size and severity of the lesion. For a large lesion about 100 ml was applied and for a small relatively minor lesion about 5 ml was applied. In some instances the composition was applied to both the lesion and the bandage. The lesion with topically applied composition was then covered by a bandage as illustrated in FIG. 1.

The animals were re-examined 3 to 8 days later and the results were recorded. A compilation of the results obtained are provided in Table 2, supra.

One of ordinary skill in the art will appreciate that the materials listed above could be substituted with others that are not identical in quality or made by the same commercial supplier. These substitutions will not necessarily affect the therapeutic activity of the composition. Therefore, the materials listed are meant to serve as one possible example from which several working variations can be made.

EXAMPLE 3

This example describes a method for making a composition containing oleum *Melaleuca alternifolia*, water-soluble *Melaleuca alternifolia*, an antimicrobial agent and a carrier. Substantially pure glycerin was obtained. Sol-U-Mel® and oleum *Melaleuca alternifolia* were both obtained from Melaleuca, Inc. A mixture comprising 73% by weight glycerin, 0.17% by weight Gentian Violet, 0.17% by weight Brilliant Green, 0.087% Proflavine hemisulfate, 12.7% by weight Sol-U-Mel® and 13.75% by weight oleum *Melaleuca alternifolia* was made. The resulting composition was placed in a high shear mixer and allowed to mix until a substantially homogenous mixture was made. The mixture was decanted into glass vials containing a stainless steel ball bearing. The ball bearing facilitated the re-distribution of the Brilliant Green, Gentian Violet and Proflavine hemisulfate in the composition. This is necessary because the Gentian Violet, Brilliant Green, and Proflavine hemisulfate settle out of the mixture.

EXAMPLE 4

This example describes a method for applying the composition containing oleum *Melaleuca alternifolia*, water-soluble *Melaleuca alternifolia*, antiseptic agent and a carrier to an animal. The animal to be treated was identified by the name of the farm and the identification tag on the animal. DD lesions were then identified. This information was then recorded along with the date of treatment.

The DD lesions were washed with Tough 'n Tender and an antibiotic liquid soap. The composition made as described in Example 2 was applied to the lesion. Amounts of the composition applied to the wound varied depending upon the size and severity of the lesion. For a large lesion about 100 ml were applied, and for a small relatively minor lesion about 5 ml were applied. In some instances the composition was applied to both the lesion and the bandage.

The animals were re-examined 3 to 8 days later and results were recorded. The results are presented in Table 3.

One of ordinary skill in the art will appreciate that the materials listed above could be substituted with others that are not identical in quality or from the same commercial supplier. These substitutions will not necessarily effect the therapeutic activity of the composition. Therefore, the materials and methods described above are meant to serve as possible examples from which several working variations can be made.

We claim all such subject matter that falls within the scope and spirit of the following claims.

What is claimed is:

1. A method for treating lesions in livestock, comprising:
   providing a composition consisting essentially of a therapeutically effective amount of oleum Melaleuca, a therapeutically effective amount of a water-soluble form of oleum Melaleuca, and a carrier, and
   applying the composition to a bandage, the bandage comprising an absorptive layer and a resilient backing; and
   contacting the lesion with bandage for a therapeutically effective period.

2. The method according to claim 1 where the composition consists essentially of:
   from about 0.2% to about 50% by weight oleum Melaleuca;
   from about 0.2% to about 50% by weight of a water-soluble form of oleum Melaleuca; and
   a carrier.

3. The method of claim 1 wherein the oleum Melaleuca is oleum *Melaleuca alternifolia*.

4. The method according to claim 1 where the composition consists essentially of:
   from about 5% to about 25% by weight oleum Melaleuca;
   from about 5% to about 25% by weight of a water-soluble form of oleum Melaleuca; and
   a carrier.

5. The method according to claim 1 where the composition consists essentially of:
   about 15% by weight oleum Melaleuca;
   about 15% by weight of a water-soluble form of oleum Melaleuca; and
   glycerin.

6. The method according to claim 1 comprising treating microbial infections.

7. A method for treating lesions in livestock, comprising:
   providing a composition consisting essentially of a therapeutically effective amount of oleum Melaleuca, a therapeutically effective amount of a water-soluble form of oleum Melaleuca, at least one additional antimicrobial agent selected from the group consisting of N-[4-[[4-(Diethylamino)phenyl]-phenylmethylen]-2,5-cyclohexadien-1-ylidene]-N-ethylethanaminium sulfate, N-[4[Bis[4-)dimethylamino)-phenyl]methylene]-2,5-cyclohexadien-1-ylidene]-N-methyl-methanaminium chloride, 3,6-Acridinediamine hemisulfate, and mixtures thereof, and a carrier; and
   applying the composition to a bandage, the bandage comprising an absorptive layer and a resilient backing; and
   contacting the lesion with bandage for a therapeutically effective period.

8. The method according to claim 7 where the composition comprises:
   from about 5% to about 25% by weight of the oleum Melaleuca;
   from about 5% to about 25% of the water-soluble form of oleum Melaleuca; and
   less than about 1% of the at least one additional antimicrobial agent.

9. The method according to claim 7 where the composition comprises:
   from about 10% to about 20% by weight of the oleum Melaleuca;
   from about 10% to about 20% by weight of the water-soluble form of oleum Melaleuca;
   from about 0.05% to about 5% by weight N-[4-[[4-(Diethylamino)phenyl]-phenylmethylene]-2,5-cyclohexadien-1-ylidene]-N-ethylethan-amonium sulfate;
   from about 0.05% to about 5% by weight N-[4[Bis[4-(dimethylamino)-phenyl]methylene]-2,5-cyclohexadien-1-ylidene]-N-methyl-methanamonium chloride;
   from about 0.01% to about 5% by weight 3,6-Acridinediamine hemisulfate; and
   a carrier.

10. A method for treating lesions in livestock, comprising:
    providing a composition comprising from about 5% to about 25% by weight oleum Melaleuca, from about 5% to about 25% by weight of a water-soluble form of oleum Melaleuca, the balance being glycerin;
    applying the composition to an absorptive material having a resilient backing; and
    contacting the lesion with the absorptive material for a therapeutically effective period.

11. A method for treating lesions in livestock, comprising:
    providing a composition comprising from about 10% to about 20% by weight of oleum Melaleuca, from about 10% to about 20% by weight of a water-soluble form of oleum Melaleuca, from about 0.05% to about 5% by weight N-[4-[[4-(Diethylamino)phenyl]-phenylmethylene]-2,5-cyclohexadien-1-ylidene]-N-ethylethan-amonium sulfate, from about 0.05% to about 5% by weight N-[4[Bis[4-(dimethylamino)-phenyl]methylene]-2,5-cyclohexadien-1-ylidene]-N-methyl-methanamonium chloride, from about 0.01% to about 5% by weight 3,6-acridinediamine hemisulfate, the balance being glycerin;
    applying the composition to an absorptive material having a resilient backing; and
    contacting the lesion with the absorptive material for a therapeutically effective period.

12. The method according to claim 1 where the carrier is glycerin.

13. The method according to claim 7 where the carrier is glycerin.

* * * * *